US010631950B2

(12) United States Patent
Anderson et al.

(10) Patent No.: US 10,631,950 B2

(45) Date of Patent: Apr. 28, 2020

(54) IDENTIFYING CORRECT CONNECTIONS ON A SURGICAL CONSOLE

(71) Applicant: Novartis AG, Basel (CH)

(72) Inventors: Joshua Anderson, Keller, TX (US); Paul R. Hallen, Colleyville, TX (US)

(73) Assignee: Alcon Inc., Fribourg (CH)

(*) Notice: Subject to any disclaimer, the term of this patent is extended or adjusted under 35 U.S.C. 154(b) by 0 days.

(21) Appl. No.: 16/150,526

(22) Filed: Oct. 3, 2018

(65) Prior Publication Data

US 2019/0110862 A1 Apr. 18, 2019

Related U.S. Application Data

(60) Provisional application No. 62/573,416, filed on Oct. 17, 2017.

(51) Int. Cl.

| | |
|---|---|
| ***A61B 90/92*** | (2016.01) |
| ***A61B 90/98*** | (2016.01) |
| ***A61B 90/96*** | (2016.01) |
| *A61F 9/008* | (2006.01) |
| *A61B 17/00* | (2006.01) |
| *A61B 18/22* | (2006.01) |
| *A61B 18/00* | (2006.01) |

(52) U.S. Cl.

CPC .............. *A61B 90/92* (2016.02); *A61B 90/96* (2016.02); *A61B 90/98* (2016.02); *A61B 18/22* (2013.01); *A61B 2017/00017* (2013.01); *A61B 2017/00115* (2013.01); *A61B 2017/00199* (2013.01); *A61B 2017/00225* (2013.01); *A61B 2017/00482* (2013.01); *A61B 2017/00544* (2013.01); *A61B 2018/00988* (2013.01); *A61F 9/008* (2013.01)

(58) Field of Classification Search

CPC ......... A61B 90/92; A61B 90/96; A61B 90/98; A61B 18/22; A61B 2017/00017; A61B 2017/00115; A61B 2017/00199; A61B 2017/00225; A61B 2017/00482; A61B 2017/00544; A61B 2018/00988; A61F 9/008

See application file for complete search history.

(56) References Cited

U.S. PATENT DOCUMENTS

| | | | |
|---|---|---|---|
| 7,443,296 | B2 | 10/2008 | Mezhinsky et al. |
| 7,551,077 | B2 | 6/2009 | Raybuck et al. |
| 7,796,040 | B2 | 9/2010 | Mezhinsky et al. |

(Continued)

*Primary Examiner* — Mohamed Barakat

(57) ABSTRACT

A surgical machine comprises multiple machine connectors disposed on its face, and a device detection mechanism located close to the machine connectors. The device detection mechanism is configured to read identification data from device information component when positioned within a predetermined range. A control circuit is configured to: identify, based on a device information read from a device information component brought within the range of the device detection mechanism, a matching machine connector from multiple machine connectors, control a light source corresponding to the matching machine connector to illuminate the corresponding illumination ring with the first color, in response to this identifying, and, control the light source corresponding to each of one or more remaining ones of the machine connectors to provide no illumination or to illuminate the corresponding illumination ring with a second color.

16 Claims, 7 Drawing Sheets

105
100
125
120
130a
130b
140a
140b
126
110

(56) References Cited

U.S. PATENT DOCUMENTS

| | | | | |
|---|---|---|---|---|
| 9,498,300 | B1 * | 11/2016 | Sanchez, Jr. | A61B 90/92 |
| 2009/0121838 | A1 * | 5/2009 | Mezhinsky | A61F 9/008<br>340/10.1 |
| 2015/0148615 | A1 * | 5/2015 | Brennan | A61F 9/00736<br>600/249 |

* cited by examiner

IDENTIFYING CORRECT CONNECTIONS ON A SURGICAL CONSOLE

PRIORITY CLAIM

This application claims the benefit of priority of U.S. Provisional Patent Application Ser. No. 62/573,416 titled "IDENTIFYING CORRECT CONNECTIONS ON A SURGICAL CONSOLE", filed on Oct. 17, 2017, whose inventors are Joshua Anderson and Paul R. Hallen, which is hereby incorporated by reference in its entirety as though fully and completely set forth herein

TECHNICAL FIELD

The present disclosure relates to surgical machines and more particularly to a detection-based system for facilitating the connection of accessories to a surgical machine.

BACKGROUND

Many operations performed today involve the use of complex surgical machines. Computerized equipment is often used by surgeons in the operating room to conduct surgery. These machines monitor and implement various stages of an operation. For example, in ophthalmic surgery, computerized machines and associated tools are used by a surgeon to perform cataract removal and lens replacement. Other machines are used to perform retinal surgery. These machines allow the surgeon to proceed through the steps of an operation.

Most surgical machines are designed to work with various tools. In ophthalmic surgery, these tools include probes, scissors, hand pieces, illuminators, lasers, and consumables. These tools are designed to connect to the front console of the surgical machine. For example, a surgeon performing retinal surgery may attach a small pair of pneumatically driven scissors to the machine. The scissors, in the form of a hand piece, are connected to a pneumatic connector on the front console of the machine with a cable. The cable provides the pneumatic power required to operate the scissors. One end of the cable is attached to the scissors while the other end has a connector designed to couple with the pneumatic connector on the front console of the machine.

Typically, the front console of the machine has several connectors designed to connect with and power various tools. For example, one connector may be designed to provide pneumatic power to a tool while another connector may be designed to provide electric power to a different tool. In addition, a single pneumatic connector on the front console may be designed to interface with several different types of pneumatically-driven tools. Each tool that is plugged into the pneumatic connector will perform its intended function. One tool may be a pair of scissors used to cut tissue, while another tool may be a probe or a drug delivery device. Since each of these tools is designed to connect with the pneumatic connector on the console of the surgical machine, each is driven by the pneumatic power supplied by the machine.

During surgery, problems can arise if the wrong tool is connected to the machine. In such a case, the tool may operate normally, but the wrong procedure is performed on the patient. For example, a surgeon may mistakenly attach a pair of pneumatically-driven scissors to a machine when he intends to attach a pneumatically-driven drug delivery device. The scissors will perform their intended function of cutting tissue. Since the surgeon intended to deliver a dosage of a drug, however, the unwanted cutting performed by the scissors can injure the patient.

As another example, there may be two different types of cutting tools. Each one may interface with the same connector on the front console of the machine. Using the wrong cutting tool can inflict unintended harm on the patient. Further, there may be two different types of electrically-driven tools, such as an illuminator and a laser. Using a laser when an illuminator is required can harm the patient. Error on the part of the surgeon in using the wrong tool or the wrong type of tool can unintentionally injure a patient during an operation.

Further confusion can occur because of the labeling present on the front of a surgical machine. In conventional surgical machines, the connectors on the front console are passively labeled. A pneumatic connector designed to work with several different tools may be labeled with a single icon, symbol or a light-emitting diode (LED). This passive labeling may identify the type of connector or that power is being delivered through the connector, but such labeling may be ineffective at preventing surgeon error.

To address this problem, some conventional surgical machines employ a set of different connectors for a set of different tools. In this manner, each tool is designed to mate with its own connector. However, this configuration of numerous different connectors can be confusing to the surgeon and adds additional expense and complexity to the design of the surgical machine. Moreover, different versions of the same type of tool may interface with a single one of the connectors on the front console of the machine. For example, two different types of scissors may be adapted to fit the same pneumatic connector on the front console of the machine. Using the wrong type of scissors might harm the patient.

SUMMARY

Embodiments of the presently disclosed techniques and apparatuses may include a surgical machine that comprises a plurality of machine connectors disposed on its face, as well as a device detection mechanism (such as a radio-frequency identification (RFID) reader antenna, Bluetooth receiver, optical scanner, induction chip reader, etc.) comprising components located in proximity to the plurality of machine connectors. The device detection mechanism may be configured to detect information from compatible device information components (e.g., RFID tags, Bluetooth transmitters, bar codes, induction chips, etc.) when any of said compatible device information components is positioned within a predetermined range of the device detection mechanism. The surgical machine further comprises a plurality of illumination rings, corresponding to the plurality of machine connectors and located on the face of the surgical machine, where each illumination ring at least partially surrounds a periphery of the corresponding machine connector. Light sources corresponding to the illumination rings are also present, with each light source being integral to or adjacent to the respective illumination ring and each light source being configured to selectively illuminate the respective illumination ring with at least a first color.

The surgical machine further includes a control circuit operatively connected to the device detection mechanism and the plurality of light sources. The control circuit may identify, based on first device information read from, for example, a first compatible device information component brought within the predetermined range of the device detection mechanism, a first matching machine connector from the plurality of machine connectors. The control circuit may then control the light source corresponding to the first matching machine connector to illuminate the corresponding illumination ring with the first color (in response to said identifying). Further, the control circuit may (in response to said identifying) control the light source corresponding to each of one or more remaining ones of the machine connectors to provide no illumination or to illuminate the corresponding illumination ring with a second color.

In use, a surgical tool containing the compatible device information component may be brought near the panel with the multiple connectors. The control circuit may illuminate the illumination ring corresponding to a connector that is a proper match to this tool with a "good" color, e.g., green. Illumination rings corresponding to one or more non-matching connectors may be lit with another color, e.g., red, or with no color at all. In this manner, the person connecting the tool to the machine may be guided to the correct connector.

It is to be understood that both the foregoing general description and the following detailed description are exemplary and explanatory only and are intended to provide further explanation of the disclosure as claimed.

BRIEF DESCRIPTION OF THE FIGURES

The accompanying drawings, which are incorporated in and constitute a part of this specification, illustrate several embodiments of the disclosure and, together with the description, serve to explain the principles of the disclosure.

DETAILED DESCRIPTION

Reference is now made in detail to the exemplary embodiments of the disclosure, examples of which are illustrated in the accompanying drawings. Wherever possible, the same reference numbers are used throughout the drawings to refer to the same or like parts.

Figure 1:
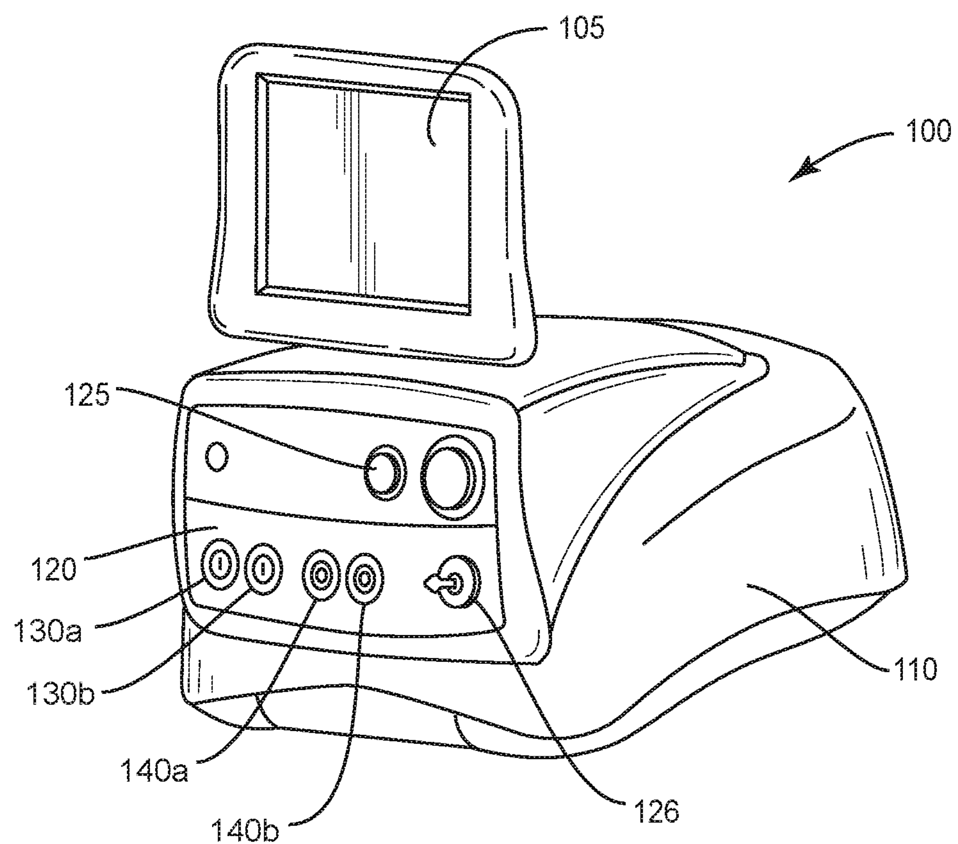
FIG. 1 is a perspective view of a surgical machine with an illumination ring system, according to an embodiment of the present disclosure.

FIG. 1 is a perspective view of an example surgical machine 100 with a device detection mechanism, according to an embodiment of the present disclosure. In FIG. 1, surgical machine 100 has a display 105 and a main surgical console 110. Information about the operation and status of surgical machine 100 may be displayed on display 105. Main surgical console 110 may include circuitry to operate surgical machine 100. Main surgical console may include a front panel 120 located on the front of surgical machine 100. Various controls, such as control knob 125 and key lock 126, may be located on front panel 120. In addition, electrical connectors and illumination rings 130 and pneumatic connectors and illumination rings 140 may be located on front panel 120. While the location of the controls 125, 126 and the connectors and illumination rings 130, 140 are shown on front panel 120, their location can be anywhere on main surgical console 110, display 105, or other peripheral.

Surgical machine 100 may also contain a device detection mechanism (e.g., an RFID reader). A typical RFID reader may include an RFID antenna, transceiver, microprocessor, power supply, and signal conditioning circuitry. The RFID reader may be installed in the surgical machine 100 so that the RFID reader is in proximity to connectors and illumination rings 130, 140. The phrase "in proximity" means that the device detection mechanism (e.g., the RFID reader) is close enough to the connectors, given the detection technology employed, to reliably detect the presence of a compatible device information component (e.g., a RFID tag) when a surgical tool's connector, containing that device information component, is brought towards any of the connectors 130, 140, before that tool's connector is plugged into one of the connectors 130, 140. Other device detection mechanisms are also contemplated. For example, a Bluetooth receiver, optical scanner, induction chip reader, etc. may be used instead of (or in addition to) an RFID reader to detect device information from a device information component on a surgical tool connector (e.g., via a compatible Bluetooth transmitter, bar code, induction chip, etc. on the tool connector). While "Bluetooth receiver" and "Bluetooth transmitter" are used herein, it is to be understood that a "Bluetooth transceiver" (which can receive and transmit Bluetooth communications) may also be used in place of "Bluetooth receiver" or "Bluetooth transmitter".

In some embodiments, the "proximity" required to illuminate the appropriate connector may be designed to be smaller than a maximum range of the detection technology utilized. For example, a field strength of the RFID or Bluetooth antenna/transmitter may be measured (or, for example, a sensitivity of the RFID or Bluetooth antenna/transmitter may be set or designed to detect at a predetermined minimum level) and matching connectors may be illuminated only when the field strength is above a level that indicates the tool connector is at least, for example, 1 foot away. Other proximity distances are also contemplated (e.g., less than 4 feet away, less than 2 feet away, less than 6 inches away, less than 3 inches away, etc.) In some embodiments, the proximity detection may prevent the surgical machine from illuminating multiple connectors when multiple surgical tools are brought near the surgical machine (e.g., when multiple tools on a tray are brought into an operating room). In some embodiments, the surgical machine may illuminate multiple connectors when multiple surgical tools are brought near the surgical machine. In some embodiments, the user may set a preference as to a maximum number of connectors to illuminate at once. In such a case, the surgical machine may illuminate the connectors based on which instruments are detected to be the closest or which instruments are detected first in time.

Figure 2:
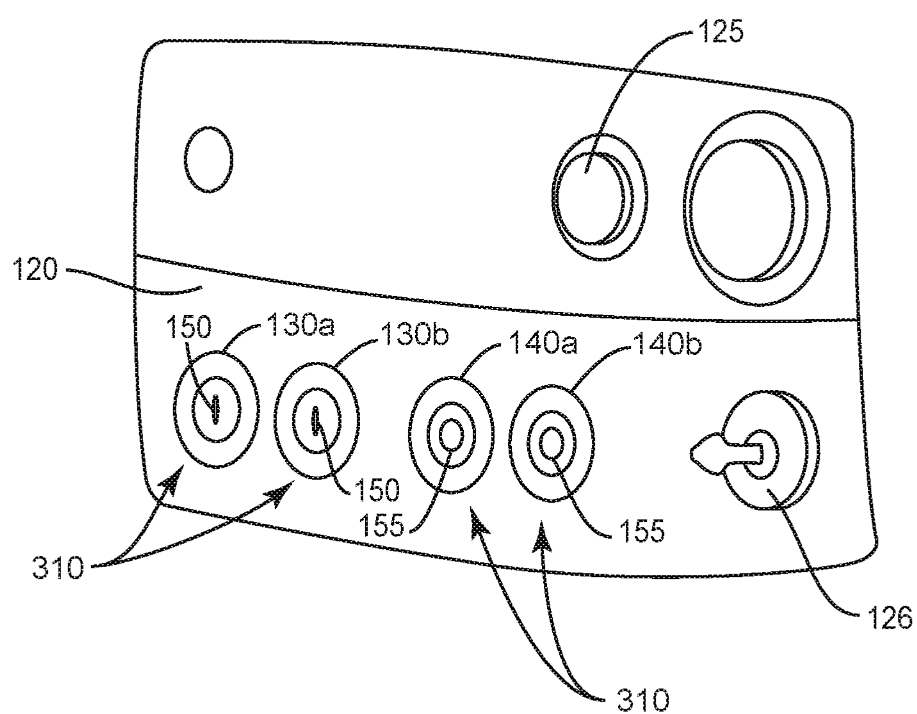
FIG. 2 is a perspective view of a front panel of a surgical machine with a device detection mechanism, according to an embodiment of the present disclosure.

FIG. 2 shows a more detailed view of the front panel 120 depicted in FIG. 1. Front panel 120 may have controls, such as control knob 125 and key lock 126. Other controls are also contemplated (e.g., push buttons, touch screens, etc.) In the embodiment shown in FIG. 2, front panel 120 has four connectors with corresponding illumination rings 130*a-b* and 140*a-b*. Electrical connectors with illumination rings 130*a-b* may each have an illumination ring 130*a-b* and an electrical connector 150. Each illumination ring 130*a-b* may be located around the periphery of the corresponding electrical connector 150. Pneumatic connectors with illumination rings 140 may each have an illumination ring 140*a-b* and a pneumatic connector 155. Each illumination ring 140*a-b* may be located around the periphery of the corresponding pneumatic connector 155. Other connector types (e.g., aspiration, irrigation, illumination/treatment laser light, etc.) with corresponding illumination rings are also contemplated. Note that while the illumination rings 130*a-b* and 140*a-b* shown in FIG. 2 completely surround their corresponding connectors, in other embodiments, one or more of the illumination rings may only partially surround the periphery of the corresponding connector or connectors.

Each of electrical connectors 150 may be configured to receive a mating connector from an electrically-powered accessory, such as a tool. When connected to an electrically-powered accessory, electrical connector 150 may provide power to that accessory. Likewise, each pneumatic connector 155 may be configured to receive a mating connector from a pneumatically-powered accessory, such as a tool. When connected to a pneumatically-powered accessory, pneumatic connector 155 may provide power to that accessory. It will be appreciated that while the example front panel illustrated in FIG. 2 includes two electrical connectors 150 and two pneumatic connectors 155, other numbers and/or types of connectors may be present in other embodiments. For example, aspiration connectors may receive mating aspiration connectors and illumination/treatment laser light connectors may receive mating illumination/treatment laser light connectors (e.g., with a mating optical fiber to convey the illumination/treatment laser light to an ophthalmic delivery tool tip).

The illumination rings 130*a-b* and 140*a-b* may be designed to display visible light in a generally ring-like configuration (other shapes are also possible). The surgical machine 100 may include a light source corresponding to each of the illumination rings 130*a-b* and 140*a-b*, where each light source may be integral to or adjacent to the respective illumination ring and may be configured to selectively illuminate the respective illumination ring with at least a first color. In some embodiments, each of one or more light sources may be configured to selectively illuminate a corresponding illumination ring with a second color, where the color of the illumination is controlled by a control signal input to the light source. In some embodiments, each light source may comprise, for example, an LED.

In various embodiments, the illumination rings 130*a-b* and 140*a-b* may be located around the periphery of the connectors (e.g., connector 305). While shown as a continuous ring, illumination rings 130*a-b* and 140*a-b* may take on other configurations. For example, illumination rings 130*a-b* and 140*a-b* may be in the shape of a square, triangle, or other polygon. In addition, the light produced by illumination rings 130*a-b* and 140*a-b* may not be continuous as shown. For example, a broken ring of light may be used. In some embodiments, the light may include flashing or pulsating light.

Figure 3:
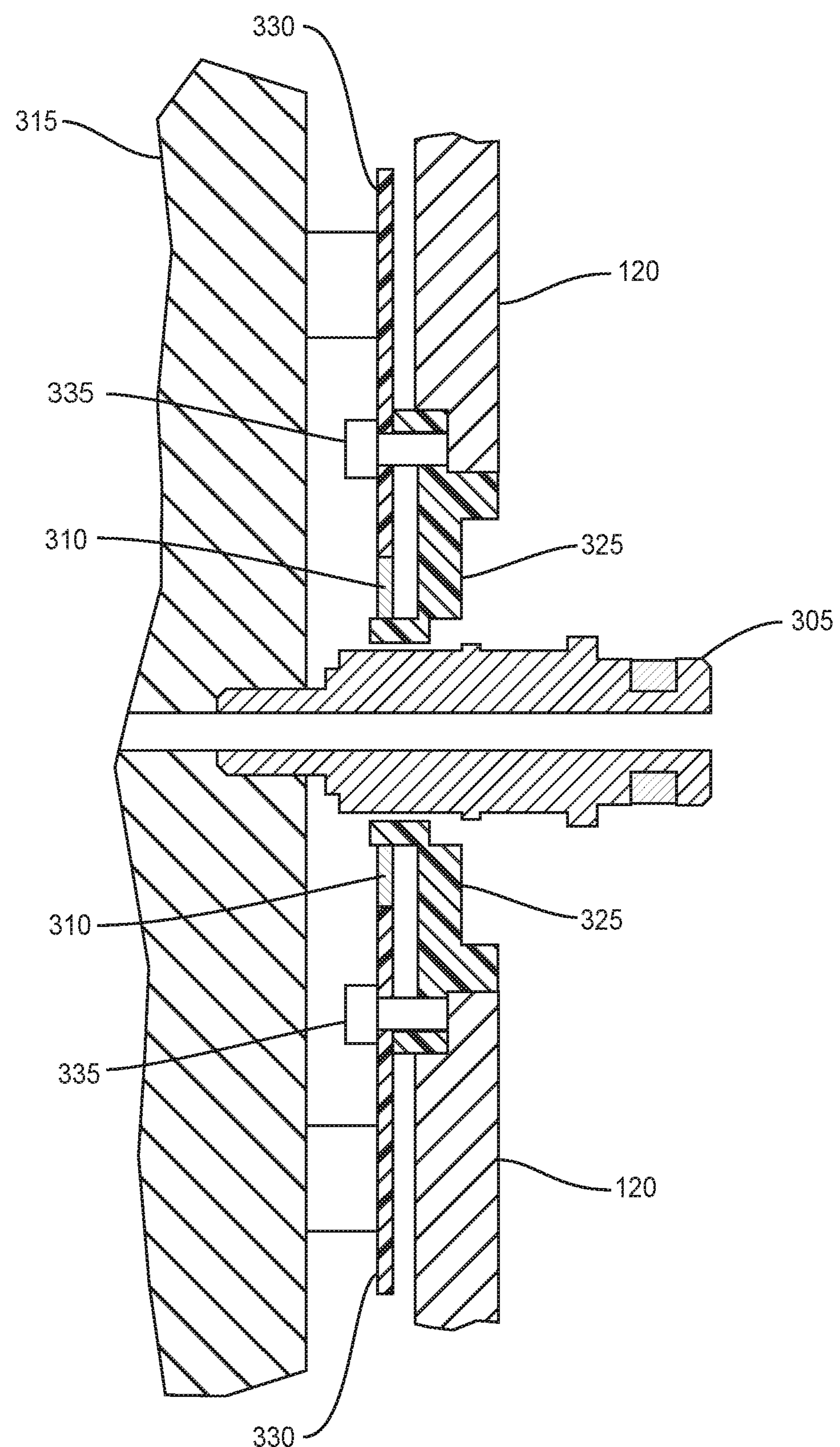
FIG. 3 is an exploded view of a connector and illumination ring on the front panel of a surgical machine with a device detection mechanism, according to an embodiment of the present disclosure.

FIG. 3 is an exploded side view of an example connector and illumination ring that may be located on front panel 120 of surgical machine 100. In FIG. 3, male connector 305 may be mounted onto manifold 315 of surgical machine 100. Manifold 315 may be located behind and attached to front panel 120 of surgical machine 100. Printed circuit board (PCB) 330 may be located between manifold 315 and front panel 120. Other arrangements of the manifold and printed circuit board are also possible.

In some embodiments, the male connector 305 may protrude through PCB 330 and front panel 120 to allow connection with a female connector on a tool. In some embodiments, the connector on the surgical machine may be a female connector and the male connector may be on the tool. Light sources 335 (e.g., LEDs) may be mounted on a side of PCB 330 that faces the manifold 315 (such that light sources 335 are mounted on the side of PCB 330 that does not face front panel 120). The light sources 335 may be mounted in other locations (e.g., the front face of the front panel, etc.)

The device detection mechanism 310 (e.g., an RFID reader, optical scanner, Bluetooth receiver, etc.) may also be located on or integrated into PCB 330. Other components of the device detection mechanism (which, for RFID detection may include one or more of an RFID transmitter circuit, an RFID receiver circuit, and an RFID control circuit), may be further embodied in one or more integrated or discrete components located on or in PCB 330 as well. In embodiments with other types of device detection mechanisms, the device detection mechanisms (e.g., including, for example, a Bluetooth receiver, optical scanner, induction chip reader, etc.) may be embodied in one or more integrated or discrete components located on or in PCB 330.

In FIG. 3, an illumination ring is thus configured to be selectively illuminated with a corresponding light source 335 comprising LEDs and lens 325, which may be considered one example of the light sources discussed above. Lens 325 may be located in front of PCB 330 and in a plane substantially parallel with front panel 120 (other locations and orientations for the lens are also contemplated). The front face of lens 325 may be visible when looking at the front panel 120. Light from light sources 335 (e.g., LEDs) may pass through holes in the PCB 330 and be refracted and diffused by lens 325. In some embodiments, the LEDs may be mounted on the front side of the PCB 330 such that the light from the LEDs does not need to pass through holes to be visible from the front of the surgical console 110. A ring of visible light may be observed when looking at the lens 325 on front panel 120. Lens 325 may refract and diffuse the light produced by light sources 335 to produce a uniform ring of light. In some embodiments, a separate lens 325 may not be used.

Additional implementation details for various embodiments of connector and illumination ring combinations may be found in U.S. Pat. No. 7,551,077, issued to Alcon, Inc. on 23 Jun. 2009 and U.S. Pat. No. 7,443,296 issued to Alcon, Inc. on Oct. 28, 2008. The entire contents of U.S. Pat. Nos. 7,551,077 and 7,443,296 are hereby incorporated by reference in their entirety as though fully and completely set forth herein for the purpose of providing additional background and implementation details that may be applied to embodiments described herein.

Figure 4:
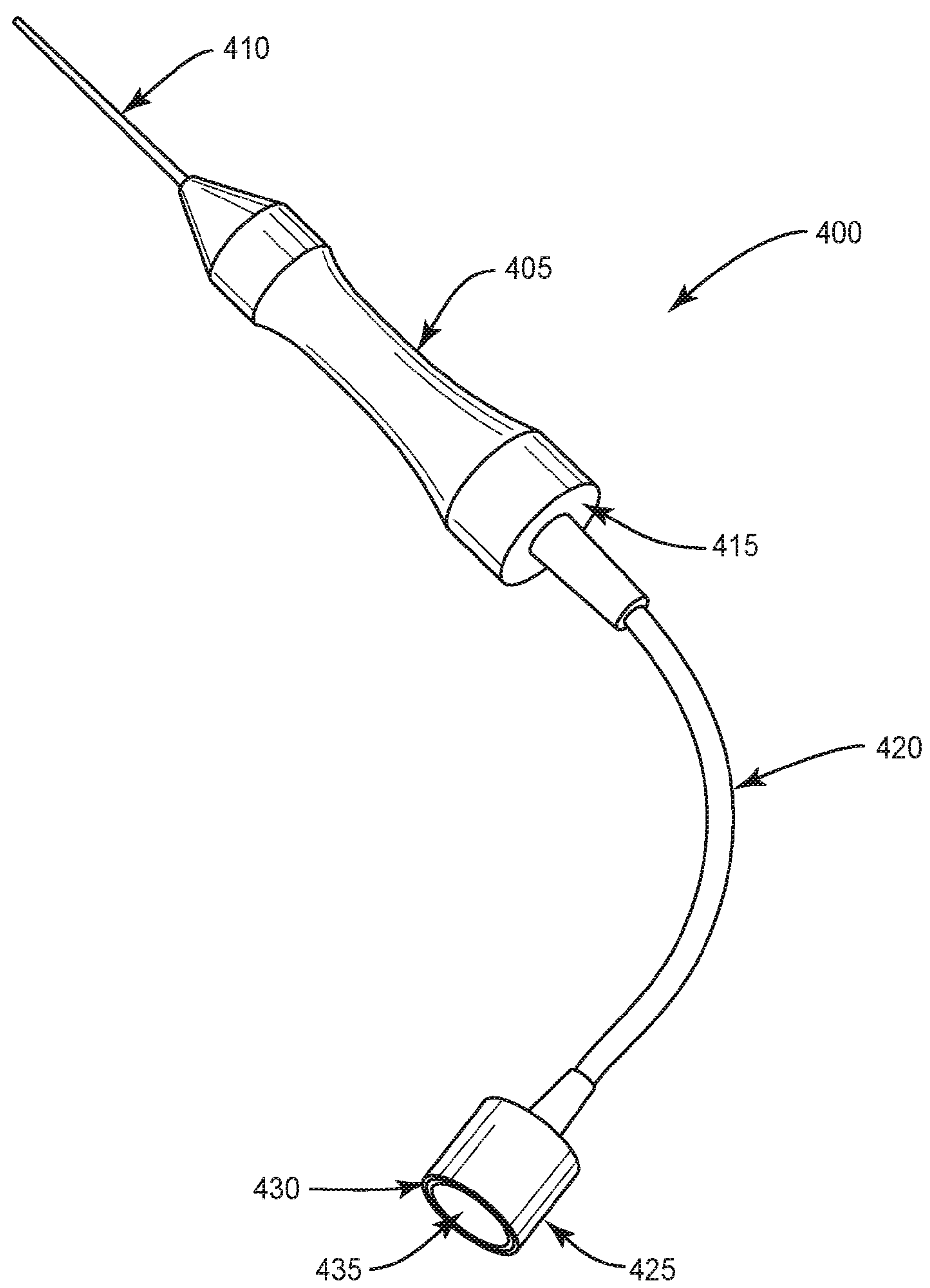
FIG. 4 is a perspective view of a tool containing a device information component for use with a surgical machine with a device detection mechanism, according to an embodiment of the present disclosure.

FIG. 4 is a perspective view of a tool containing a device information component for use with surgical machine 100. Tool 400 has a hand piece 405, cable 420, and a female connector 425. Hand piece 405 has a working tip 410 which can be any type of device used in surgery. For example, working tip 410 may be a small pair of pneumatic scissors designed to cut ocular tissue or a drug delivery device designed to place a quantity of drug in the posterior of an eye. Cable 415 connects to hand piece 405 on surface 415.

Cable 420 extends from surface 415 of hand piece 405 to female connector 425. Cable 420 may attach to female connector 425 on a surface opposite receiving cavity 435. In some embodiments, cable 420 may be configured to provide electrical power to hand piece 405 and working tip 410. In some embodiments, cable 420 is configured to provide pneumatic power to hand piece 405 and working tip 410. Cable 420 may help to control hand piece 405 and working tip 410, such as by varying levels of power. In this manner, cable 420 could be used to both power and control hand piece 405 and working tip 410. Other hand piece types are also contemplated (e.g., an irrigation/aspiration handpiece (with or without a phacoemulsification tip) or an illumination/treatment laser hand piece).

Female connector 425 may have a generally cylindrical shape. Female connector 425 may have a receiving cavity 435 configured to fit male connector 305. In this manner, the receiving cavity 435 on connector 425 has a female configuration, and male connector 305 has a male configuration. When connected, surgical machine 100 may deliver one or more of electrical power, pneumatic air, aspiration, irrigation, light energy, etc. to tool 400. While female connector 425 is shown with a female configuration, it is understood that any suitable configuration can be used. For example, female connector 425 can be reconfigured to have a male configuration, and male connector 305 can be reconfigured to have a female configuration.

Female connector 425 may also have a device information component 430 (such as an RFID tag, bar code for an optical scanner, Bluetooth transmitter, etc.) disposed near receiving cavity 435 (e.g., on a surface around receiving cavity 435). In the case of an RFID device detection mechanism, the RFID tag may be compatible, i.e., readable by, an RFID reader in surgical machine 100. The location of the device information component 430 may place the device information component 430 close to front panel 120 shortly before and during the connecting of female connector 425 to male connector 305. In this manner, the device information component 430 may be placed in close proximity to the device detection mechanism 310 on the surgical machine during the process of bringing the female connector 425 towards the front panel 120 for connecting to one of the several connectors on the front panel. In the illustrated example, the device information component 430 (e.g., an RFID tag) may have a circular configuration. In some embodiments, the device detection mechanism 310 may have a similar configuration (e.g., RFID reader antenna may have a circular configuration). While shown as having a circular configuration, any configurations can be used without departing from the scope of the present disclosure.

In some embodiments, the device information component 430 may not be placed near the surface of the receiving cavity 435. For example, a Bluetooth transmitter may be placed anywhere along the tool 400 (e.g., inside the connector 425 or inside the hand piece 405). As another example, a bar code may be placed on the side of connector 425 such that an optical scanner near the male connector 305 may read the bar code as the bar code nears the connector 305. The distance to the tool may be determined by the size of the bar code detected by the optical scanner. Other device information components are also contemplated.

Figure 5:
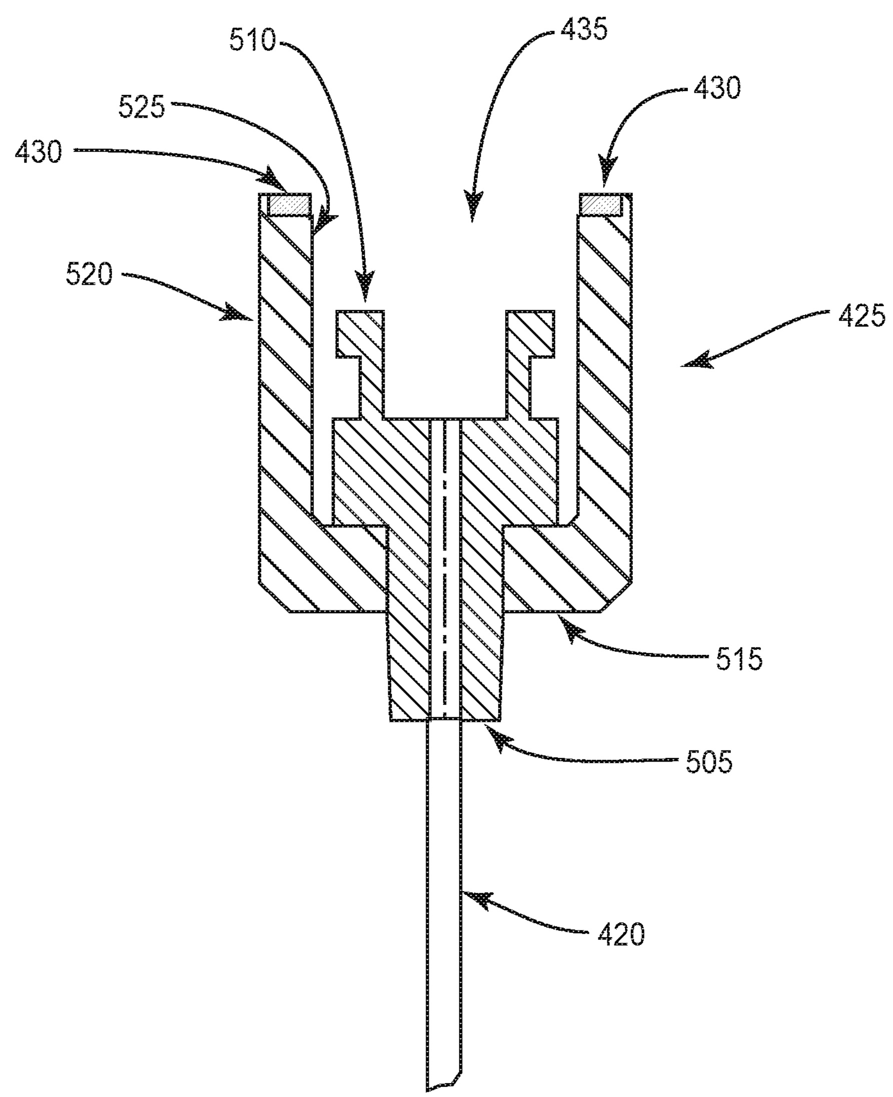
FIG. 5 is an exploded cross-section view of a connector on a tool for use with a surgical machine with a device detection mechanism, according to an embodiment of the present disclosure.

FIG. 5 is an exploded cross-section view of the female connector 425 depicted in FIG. 4. Female connector 425 may have a generally cylindrical shape. Other shapes are also contemplated (e.g., square, oval, etc.) Surface 505 and surface 515 may be generally parallel. Other profiles are contemplated (e.g., surface 505 and/or surface 515 may be cone shaped or tapered). Cable 420 may extend from surface 505 outward toward hand piece 405. Cable 420 may also extend inward from surface 505 to enable the necessary internal connections with female connector 425. In this manner, electrical power, pneumatic air, aspiration, irrigation, light energy, etc. may be delivered from surgical machine 100 through male connector 305 to female connector 425 through cable 420 and to hand piece 405. For example, if hand piece 405 is a phacoemulsification hand piece, electrical power supplied through connector 425 may power a phacoemulsification tip (or be used in some other way by working tip 410).

In this example configuration, device information component 430 may be arranged circularly around receiving cavity 435 on a surface opposite surface 515. Alternatively, device information component 430 can be disposed on exterior surface 520, interior surface 525, or some other location near receiving cavity 435. For example, a bar code may be placed on the outside of surface 520. Female connector 425 is also shown with member 510 configured to connect with male connector 305. When female connector 425 is brought into proximity of the front panel 120, for example during the process of connecting female connector 425 to male connector 405, device information component 430 may be located close to device detection mechanism 310.

In the case of an RFID device detection mechanism, an RFID reader antenna and corresponding RFID tag may communicate with each other when brought into close proximity to each other. RFID reader antenna may emit an RF (radio frequency) field. When female connector 425 with RFID tag is brought within this field, communication may be established between RFID tag and RFID reader antenna. It is not necessary that female connector 425 and male connector 305 actually be coupled together for communication to take place. This is also the case for other types of device detection mechanisms (e.g., an optical reader in the console can read a bar code on the hand piece or a Bluetooth transmitter on the hand piece can communicate with a Bluetooth receiver in the console without the female and male connectors being connected).

Figure 6:
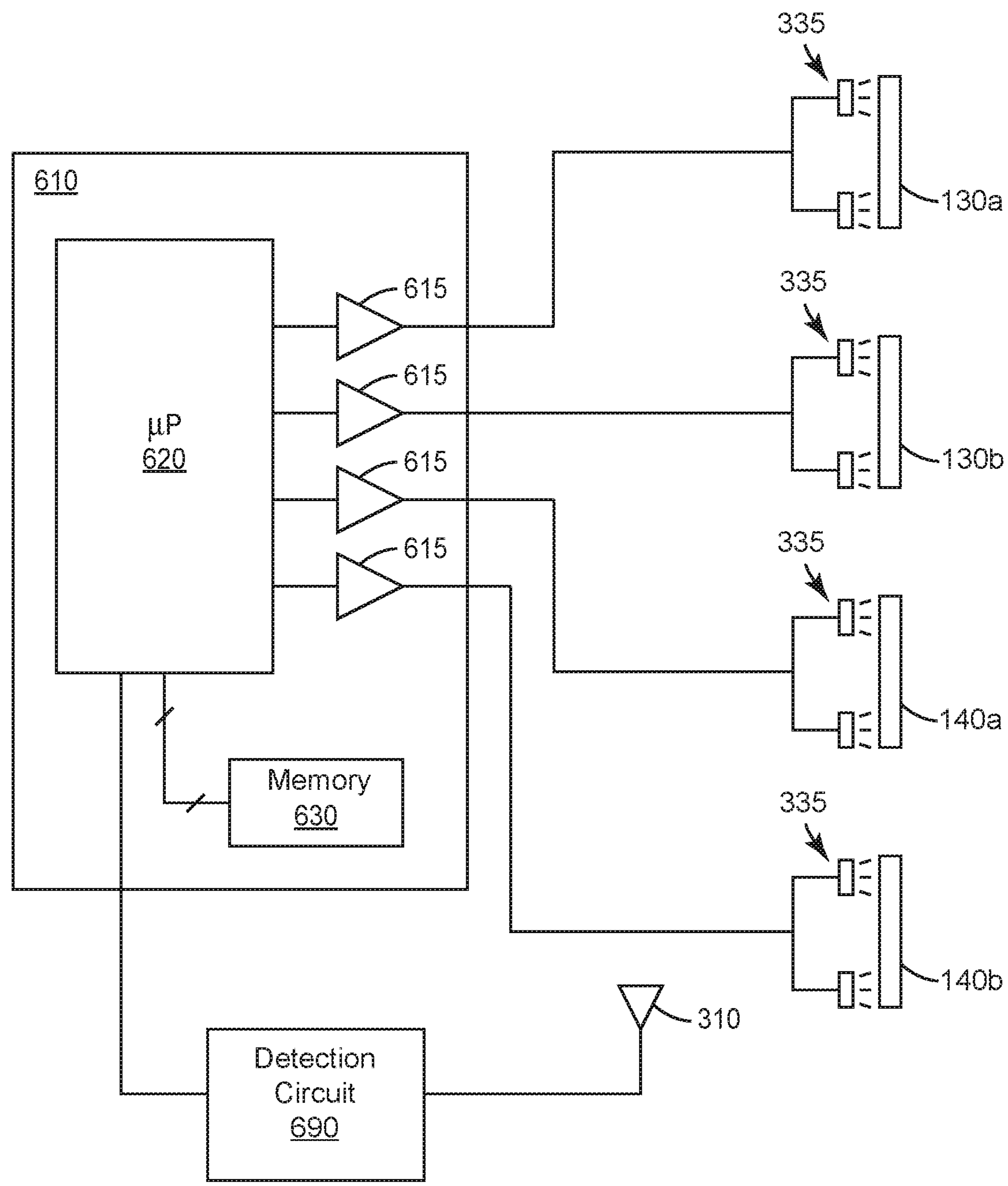
FIG. 6 is an exploded cross-section view of a connector and an illumination ring on the front panel of a surgical machine with a device detection mechanism coupled to a connector on a tool for use with a surgical machine with a device detection mechanism, according to an embodiment of the present disclosure.

FIG. 6 is a schematic diagram illustrating an example control circuit 610 arranged to control the selective illumination of light sources 335, where each of the illustrated light sources 335 corresponds to a respective illumination ring 130*a-b* and 140*a-b*. Control circuit 610 comprises a microprocessor or microcontroller 620, operatively connected to a memory 630, where memory 630, which may comprise one or more of a random-access memory (RAM), read-only memory (ROM), flash memory, or the like, stores program instructions for execution by microprocessor 620, whereby microprocessor 620 is configured to carry out one or more of the techniques and operations described herein. The microprocessor 620 may receive signals from the detection circuit 690 which in turn may utilize a device detection mechanism 310. For example, in embodiments using RFID for the information detection, microprocessor 620 may be connected to an RFID circuit (an embodiment of a detection circuit 690), which in turn may be connected to an RFID reader (an embodiment of a device detection mechanism 310), positioned in proximity to the illumination rings 130*a-b* and 140*a-b*. Microprocessor 620 may thus be configured to receive signals from detection circuit 690 indicating when a compatible RFID tag is brought within the reading range of detection circuit 690 and providing to the microprocessor 620, for example, identification data read from the RFID tag by the device detection mechanism 310.

According to several embodiments of the present disclosure, control circuit 610 is thus configured to identify, based on device information read from a device information component 430 (brought within the predetermined range of the device detection mechanism 310) a matching machine connector from the plurality of machine connectors corresponding to light sources 335 and illumination rings 130*a-b* and 140*a-b*. In some embodiments, this identification may be based on other information in addition to the device information. For example, the identification of the matching machine connector may be based on an indication of use or function of the tool. In some embodiments, this indication of use or function of the tool may be read from the device information component 430 along with the device information; in other embodiments the use or function information may be retrieved from some other source, e.g., from a table stored in memory and/or from an external source, e.g., via a network connection.

After identifying the matching machine connector, the control circuit 610 may be further configured to control the light source 335 corresponding to this matching machine connector to illuminate the corresponding illumination ring (e.g., one or more specific illumination rings of the four illumination rings 130*a-b* and 140*a-b*) with a color, in response to this identification, such that the color of the illumination and/or the presence of the illumination indicates that the matching machine connector is an appropriate match for the tool connector that contains the device information component 430 that has just been read. The control circuit 610 may be further configured to, in response to this identification, control the light source corresponding to each of one or more remaining ones of the machine connectors to provide no illumination or to illuminate the remaining ones of the non-matching illumination rings with a second color (e.g., red or amber), where this second color, if used, indicates that the non-matching machine connectors are not an appropriate match for the tool connector that contains the device information component 430 that has just been read.

In some embodiments, the illumination ring corresponding to the at least one correct machine connector may be illuminated with the first color, e.g., with a green light, to indicate that the machine connector is an appropriate match for the tool connector that has been brought into close proximity of the connectors. In some embodiments or instances, there may be more than one appropriate match, in which case more than one illumination ring may be illuminated with the first color in response to the proximity of the tool connector. For example, if the connector is for a pneumatic tool as indicated by the information detected from the device information component 430, the illumination rings for the pneumatic connectors may illuminate green. For example, if both illumination rings 140*a-b* correspond to pneumatic connectors, both illumination rings 140*a-b* may illuminate green.

Illumination rings corresponding to machine connectors that are not an appropriate match, on the other hand, are either not illuminated, in some embodiments, or illuminated with a second color, in other embodiments, where the second color indicates that the corresponding machine connectors are not appropriate matches. For example, in some embodiments the illumination rings for the one or more matching connectors may be illuminated with a green color, to indicate a match, while the illumination rings for one or more other connectors may be illuminated with a red or amber color (or some other color), to indicate that the corresponding connectors are not good matches for the surgical tool that is being connected. In the pneumatic example provided above, while both illumination rings 140*a-b* for the pneumatic connectors may illuminate green, both illumination rings 130*a-b* for the electronic connectors may illuminate, for example, red (or not illuminate at all). In various embodiments, the light sources 335 may be configured to selectively illuminate the respective illumination rings 130*a-b* and 140*a-b* with one of the two colors, under the control of the control circuit 610. Other illumination schemes are also contemplated.

It should be noted that in some embodiments where the control circuit 610 is configured to control one or more of the illumination rings 130*a-b* and 140*a-b* to illuminate with the second color, where the second color indicates an inappropriate match, one or more illumination rings 130*a-b* and 140*a-b* may remain unilluminated. This might be done, for example, for an illumination ring corresponding to a machine connector that is already occupied by a tool connector, or for an illumination ring corresponding to a machine connector that has been inactivated (e.g., due to a detected fault condition).

As indicated above, the control circuit 610 may be configured to identify the (at least one) matching connector based on the device information read from the device information component 430 on the tool connector 425 brought into the vicinity of the front panel, and hence into the vicinity of the device detection mechanism 310. Thus, after identifying the machine connector (e.g., one of connectors 150 or 155) corresponding to the tool connector and illuminating the corresponding illumination ring, as discussed above, the control circuit described above may be further configured to identify, based on a differing device information read from a second device information component 430 brought within the predetermined range of the device detection mechanism 310, a second matching machine connector from the plurality of machine connectors, and to control the light source corresponding to the second matching machine connector to illuminate the corresponding illumination ring with the first color, in response to this identifying of the second matching machine connector. The control circuit 610 in these embodiments may be further configured to, in further response to this identifying of the second matching machine connector, control the light source corresponding to each of one more of the machine connectors other than the second matching machine connector to provide no illumination or to illuminate the corresponding illumination ring with the second color, depending on the embodiment.

It will be appreciated that different device information, on the tool connectors 425 for different types of tools 400, may correspond to different ones of the machine connectors 150,155 on the front of the panel. This association between the machine connectors 150,155 and the device information may be static, in that it doesn't change from one use of the machine to another, or dynamic, in that the surgical machine 100 may be reconfigured for different procedures, from time to time, such that the association between machine connectors 150,155 and the device information for the tools 400 may depend on the specific operational configuration of the surgical machine 100. In either case, this association between machine connectors 150,155 and device information for tools 400 may be stored in the memory 630 of the control circuit 610.

The types of machine connectors 150,155 may vary, from one machine to another, or from one connector to another, on the same machine. In some embodiments, one or more of the machine connectors 150,155 may be connected to an electric power supply circuit in the surgical machine and may be configured to deliver electrical power to a surgical tool 400 connected to the machine connector 150,155. In some of these and/or in other embodiments, one or more of the machine connectors 150,155 may be configured to deliver pneumatic power (or, for example, hydraulic power) to a surgical tool 400 connected to the machine connector 150, 155. In some of these and/or in still other embodiments, one or more of the machine connectors 150,155 may be configured to deliver aspiration or irrigation to a surgical tool 400 connected to the machine connector 150,155. In some embodiments, each of one or more of the machine connectors 150,155 may be optically connected to a laser light source, and may be configured to deliver light from the laser light source to a surgical tool 400 connected to the machine connector 150,155.

In view of the detailed examples described above and illustrated in the attached drawings, it will be appreciated that embodiments of the present disclosure include several variations of a surgical machine 100 that include a plurality of machine connectors 150,155 disposed on a face of the surgical machine 100, and an detection circuit 690 comprising a device detection mechanism 310 located in proximity to the plurality of machine connectors 150,155, where the detection circuit 690 is configured to read information (e.g., identification data) from device information component 430 when any of said device information component 430 is positioned within a predetermined range of the device detection mechanism 310. These embodiments further include a plurality of illumination rings 130*a-b* and 140*a-b* corresponding to the plurality of machine connectors 150, 155 and located on the face of the surgical machine 100, with each illumination ring at least partially surrounding a periphery of the corresponding machine connector, as well as a plurality of light sources 335 corresponding to the plurality of illumination rings 130*a-b* and 140*a-b*, where the light source 335 may be integral to or adjacent to the respective illumination ring and may be configured to selectively illuminate the respective illumination ring with at least a first color.

Figure 7:
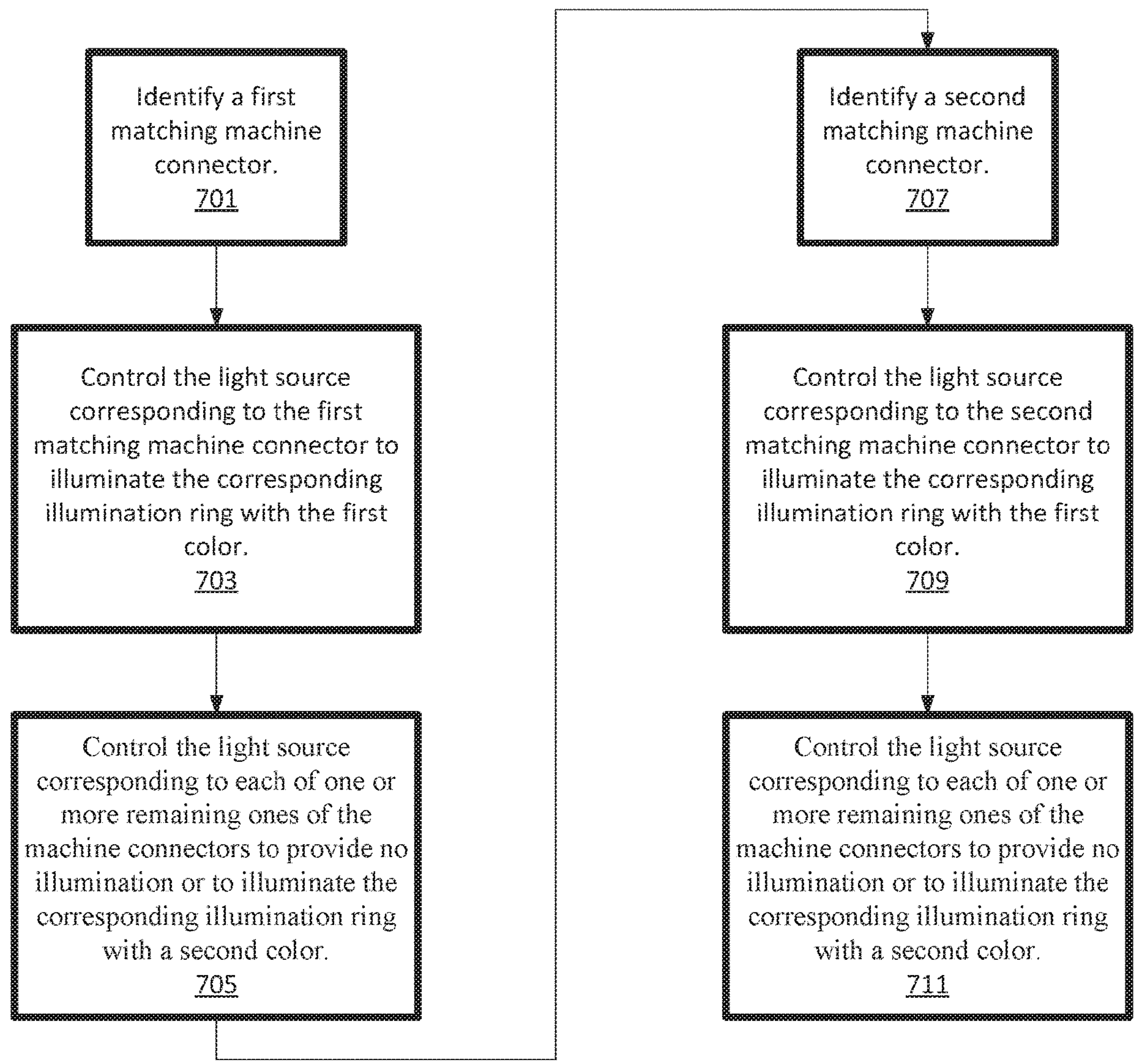
FIG. 7 illustrates a flowchart of a method for device information identification, according to an embodiment.

FIG. 7 illustrates a flowchart of a method for device information identification, according to an embodiment. A control circuit 610 may be operatively connected to the detection circuit 690 and the plurality of light sources 335, and may be configured to perform one or more elements described herein.

At 701, the control circuit may identify, based on a first device information read from a first device information component 430 brought within the predetermined range of the device detection mechanism 310, a first matching machine connector from the plurality of machine connectors.

At 703, the control circuit may control the light source corresponding to the first matching machine connector to illuminate the corresponding illumination ring with the first color, in response to this identification.

At 705, in response to this identification, the control circuit may control the light source corresponding to each of one or more remaining ones of the machine connectors to provide no illumination or to illuminate the corresponding illumination ring with a second color.

A surgical machine 100 according to any of these embodiments may be configured to recognize any of several different tools or types of tools 400, based on the device's information provided by the device information component 430 installed in, on, or near the surgical tool's connector 425. Thus, in some embodiments the control circuit 610 may be further configured to perform the following elements.

At 707, the control circuit may identify, based on a differing device information read from a second device information component 430 brought within the predetermined range of the device detection mechanism 310, a second matching machine connector from the plurality of machine connectors.

At 709, the control circuit may control the light source 335 corresponding to the second matching machine connector to illuminate the corresponding illumination ring with the first color, in response to this identifying of the second matching machine connector. In some embodiments, upon detecting a differing device information, the machine connectors may be illuminated according to the newly detected differing device information such that the previous illuminated rings for the first device information may no longer be illuminated (to avoid confusion as the user attempts to connect the second connector).

At 711, the control circuit, in response to this identifying of the second matching machine connector, may control the light source corresponding to each of one more of the machine connectors other than the second matching machine connector to provide no illumination or to illuminate the corresponding illumination ring with the second color. In some embodiments, upon the second device corresponding to the differing device information being correctly placed, the console may switch to illuminating only the illumination rings around the first matching machine connector (for the connector corresponding to the first device information) and the second matching machine connector (for the connector corresponding to the differing device information). The first matching machine connector and the second matching machine connector may thus be illuminated in a first color (if both connections are correct) throughout the surgery to allow users of the console to visually confirm correct connection at any time. Further, should one of the first matching machine connector or the second matching machine connector be connected to an incorrect connector, a second color may remain illuminated around that connector (and one or more warnings (such as a visual warning on display 105 and or an audible warning from the console) may continue until the incorrect connector is removed).

A surgical system may comprise any of the surgical machines described above in combination with at least one surgical tool, the surgical tool 400 comprising a hand-piece 405, a cable 420 having a first end connected to the hand-piece 405, and a tool connector 425 attached to a second end of the cable 420. In these embodiments, the tool connector 425 may be configured to mate with at least one of the machine connectors 150,155 disposed on the face of the surgical machine, and the surgical tool may further comprise a device information component 430 disposed in, on, or near the tool connector, where the device information component 430 is compatible with the detection circuit 690. The surgical tool 400 may further comprise a device detection mechanism 310 and associated circuitry configured to communicate tool device information to the detection circuit 690 when the device information component 430 is positioned within the predetermined range (e.g., within 4 feet, within 2 feet, within 1 foot, within 6 inches, within 3 inches, etc.) of the device detection mechanism 310 and interrogated by the detection circuit 690. In some embodiments, the predetermined range may be preprogrammed into the control circuit 610 (or other portion of the surgical console 110). In some embodiments, the user may set a preferred predetermined range (e.g., using a graphical user interface on display 105).

From the above, it may be appreciated that the present disclosure provides an improved RFID illumination ring system for use on a surgical machine. The present disclosure helps to prevent surgeon error by utilizing a device detection mechanism to determine not only whether the proper tool is connected to the surgical machine, but also by guiding the user to properly connect the tool. The present disclosure is illustrated herein by example, and various modifications may be made by a person of ordinary skill in the art.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A surgical machine, comprising:

a plurality of machine connectors disposed on a face of the surgical machine;

a detection circuit configured to detect identification data from device information components;

a plurality of illumination rings corresponding to the plurality of machine connectors and located on the face of the surgical machine, each illumination ring at least partially surrounding a periphery of the corresponding machine connector;

a plurality of light sources corresponding to the plurality of illumination rings, each light source being integral to or adjacent to the respective illumination ring and each light source being configured to selectively illuminate the respective illumination ring with at least a first color; and a control circuit operatively connected to the detection circuit and the plurality of light sources, the control circuit being configured to:

identify, based on a first device information read from a first device information component, a first matching machine connector from the plurality of machine connectors, control the light source corresponding to the first matching machine connector to illuminate the corresponding illumination ring with the first color, in response to said identifying, further in response to said identifying, control the light source corresponding to each of one or more remaining ones of the machine connectors to provide no illumination or to illuminate the corresponding illumination ring with a second color, identify, based on a differing device information read from a second device information component, a second matching machine connector from the plurality of machine connectors, control the light source corresponding to the second matching machine connector to illuminate the corresponding illumination ring with the first color, in response to said identifying of the second matching machine connector, and further in response to said identifying of the second matching machine connector, control the light source corresponding to each of one or more of the machine connectors other than the second matching machine connector to provide no illumination or to illuminate the corresponding illumination ring with the second color.

2. The surgical machine of claim 1, wherein the detection circuit is coupled to a device detection mechanism configured to read information from the first and second device information components when the first and second device information components are brought within a predetermined range of the device detection mechanism.

3. The surgical machine of claim 2, wherein the device detection mechanism is a Radio Frequency identification (RFID) reader and at least one of the first device information component and the second device information component is an RFID tag.

4. The surgical machine of claim 2, wherein the device detection mechanism is an optical scanner and at least one of the first device information component and the second device information component is a bar code.

5. The surgical machine of claim 2, wherein the device detection mechanism is a Bluetooth receiver and at least one of the first device information component and the second device information component is a Bluetooth transmitter.

6. The surgical machine of claim 2, wherein the device detection mechanism is an induction chip reader and at least one of the first device information component and the second device information component is an induction chip.

7. The surgical machine of claim 1, wherein each of one or more of the machine connectors is electrically connected to a power supply circuit in the surgical machine and is configured to deliver electrical power to a surgical tool connected to the machine connector.

8. The surgical machine of claim 1, wherein each of one or more of the machine connectors is configured to deliver pneumatic power to a surgical tool connected to the machine connector.

9. The surgical machine of claim 1, wherein each of one or more of the machine connectors is configured to deliver hydraulic power to a surgical tool connected to the machine connector.

10. The surgical machine of claim 1, wherein each of one or more of the machine connectors is optically connected to a laser light source, and is configured to deliver light from the laser light source to a surgical tool connected to the machine connector.

11. A surgical system comprising the surgical machine of claim 1 and further comprising a surgical tool, the surgical tool comprising a hand-piece, a cable having a first end connected to the hand-piece, and a tool connector attached to a second end of the cable, wherein the tool connector is configured to mate with at least one of the machine connectors disposed on the face of the surgical machine and wherein the surgical tool further comprises a device information component disposed in, on, or near the tool connector, the device information component being compatible with the detection circuit and a device detection mechanism coupled to the detection circuit, and the device information component is configured to communicate a tool device information to the detection circuit when the device information component is positioned within a predetermined range of the device detection mechanism and interrogated by the detection circuit.

12. A method, comprising:

identifying, based on a first device information read from a first compatible device information component brought within a predetermined range of a device detection mechanism, a first matching machine connector from a plurality of machine connectors;

controlling a light source corresponding to the first matching machine connector to illuminate an illumination ring corresponding to the first matching machine connector with a first color, in response to said identifying;

in further response to said identifying the first matching machine connector, controlling one or more additional light sources corresponding to each of one or more remaining ones of the machine connectors to provide no illumination or to illuminate one or more additional illumination rings corresponding to the one or more remaining ones of the machine connectors with a second color;

identifying, based on a differing device information read from a second compatible device information component brought within the predetermined range of the device detection mechanism, a second matching machine connector from the plurality of machine connectors;

controlling a light source corresponding to the second matching machine connector to illuminate an illumination ring corresponding to the second matching machine connector with the first color, in response to said identifying of the second matching machine connector; and in further response to said identifying the second matching machine connector, controlling the light sources corresponding to each of one or more of the machine connectors other than the second matching machine connector to provide no illumination or to illuminate the corresponding illumination rings with the second color.

13. The method of claim 12, wherein at least one of the first compatible device information component and the second compatible device information component is a radio-frequency identification (RFID) tag and the device detection mechanism is a RFID reader.

14. The method of claim 12, wherein at least one of the first compatible device information component and the second compatible device information component is a bar code and the device detection mechanism is an optical scanner.

15. The method of claim 12, wherein at least one of the first compatible device information component and the second compatible device information component is a Bluetooth transmitter and the device detection mechanism is a Bluetooth receiver.

16. The method of claim 12, wherein at least one of the first compatible device information component and the second compatible device information component is an induction chip and the device detection mechanism is an induction chip reader.

* * * * *